(12) United States Patent
Venaille et al.

(10) Patent No.: US 8,522,982 B2
(45) Date of Patent: Sep. 3, 2013

(54) METHOD AND DEVICE FOR INSPECTING TRANSPARENT OR TRANSLUCENT ARTICLES IN ORDER TO OPTIMIZE THE OPERATION OF A CONTROL MACHINE

(75) Inventors: Christophe Venaille, St-Genis Laval (FR); Laurent Barel, Condrieu (FR)

(73) Assignee: Tiama, Vourles (FR)

( * ) Notice: Subject to any disclaimer, the term of this patent is extended or adjusted under 35 U.S.C. 154(b) by 525 days.

(21) Appl. No.: 12/599,359

(22) PCT Filed: May 9, 2008

(86) PCT No.: PCT/FR2008/050818
§ 371 (c)(1),
(2), (4) Date: Jul. 19, 2010

(87) PCT Pub. No.: WO2008/149010
PCT Pub. Date: Dec. 11, 2008

(65) Prior Publication Data
US 2010/0282650 A1 Nov. 11, 2010

(30) Foreign Application Priority Data
May 9, 2007 (FR) ..................................... 07 54944

(51) Int. Cl.
*B07C 5/00* (2006.01)
(52) U.S. Cl.
USPC ........... 209/552; 209/523; 209/524; 209/557; 209/571; 209/576
(58) Field of Classification Search
USPC ................. 209/552, 523, 524, 526, 530, 557, 209/571, 576, 582
See application file for complete search history.

(56) References Cited

U.S. PATENT DOCUMENTS

| | | | |
|---|---|---|---|
| 3,386,575 A | 6/1968 | Quinn | |
| 3,941,686 A * | 3/1976 | Juvinall | 209/523 |
| 4,437,563 A * | 3/1984 | Oriol | 198/810.02 |

(Continued)

FOREIGN PATENT DOCUMENTS

| | | |
|---|---|---|
| DE | 3324449 A1 | 1/1985 |
| DE | 4302656 C1 | 5/1994 |

(Continued)

*Primary Examiner* — Terrell Matthews
(74) *Attorney, Agent, or Firm* — Clark & Brody

(57) ABSTRACT

The invention relates to a method for inspecting, with the aid of a machine (1), transparent or translucent hollow articles (Aj) streaming past a series of monitoring stations each comprising at least one sensor (Ci) delivering an output signal (Si(j)) for each article (Aj) traveling past a sensor.
According to the invention, the method consists in implementing at least one phase of assessing the setting of the machine consisting:
- in choosing compliant and defective reference articles (A'(j)),
- for each reference article (A'(j)), recording the output signals (S'i(j)) of the sensors with each of which are associated an identifier for the reference article concerned and an expected result (R'a(j)),
- in selecting together, during the processing of the signals, at least two recorded output signals [S'a(j)], [S'k(j)] corresponding to one and the same reference article, so as to obtain after processing, a result (R'j),
- and in comparing the result obtained by processing (R'j) regarding the defective or compliant character of each reference article with the expected result (Ra'(j)).

15 Claims, 4 Drawing Sheets

(56) References Cited

U.S. PATENT DOCUMENTS

| | | | |
|---|---|---|---|
| 4,931,632 A * | 6/1990 | Brandt | 250/223 B |
| 5,510,620 A | 4/1996 | Achter et al. | |
| 5,726,887 A * | 3/1998 | Spies et al. | 701/29.1 |
| 6,237,418 B1 * | 5/2001 | Coughlin et al. | 73/579 |
| 6,446,493 B1 * | 9/2002 | Lehmann | 73/49.3 |
| 6,448,549 B1 | 9/2002 | Safaee-Rad | |
| 7,402,178 B2 * | 7/2008 | Burke et al. | 8/137 |
| 2005/0263443 A1 | 12/2005 | Martin et al. | |

FOREIGN PATENT DOCUMENTS

| | | |
|---|---|---|
| DE | 19946080 A1 | 5/2000 |
| EP | 0669528 A1 | 8/1995 |
| EP | 1498724 A1 | 1/2005 |
| EP | 1560018 A1 | 8/2005 |
| WO | 02/01207 A1 | 1/2002 |

\* cited by examiner

METHOD AND DEVICE FOR INSPECTING TRANSPARENT OR TRANSLUCENT ARTICLES IN ORDER TO OPTIMIZE THE OPERATION OF A CONTROL MACHINE

The present invention relates to the technical field of the optical monitoring of translucent or transparent objects with a view to detecting defects, if any, exhibited by these articles.

The subject of the invention finds a particularly advantageous application in respect of optical inspection or monitoring with a view to detecting defects apt to appear on articles such as glass or plastic containers.

In the prior art, it is known to inspect automatically and on-line, with the aid of a monitoring machine, articles streaming at high speed past a series of monitoring stations each comprising at least one for example measurement sensor delivering an output signal for each article traveling past said sensor. High-speed streaming such as this signifies that a sensor is able to see at least one article pass by before the previous article goes past the last sensor when considering the direction of streaming of the articles. Each monitoring station checks that each article adheres to at least one quality criterion such as for example, geometric characteristics, the absence of a type of defect or, as indicated in patent application WO 02/01207, the presence of foreign bodies inside the article.

The monitoring station is provided with means for detecting the presence of an article making it possible to trigger the acquisition of a signal corresponding to the passage of each article. Each measurement sensor thus delivers an output signal which is processed so as to obtain characteristic measurements for each article. Each of these characteristic measurements is compared with a quality criterion or a setting so as to determine whether the article is compliant or defective. When an article is considered to be defective, the information is dispatched to a sorting station which is placed on the line after the last monitoring station. Of course, the advance of the articles past the various monitoring stations is tracked in such a way that the sorting station can eject the article considered to be defective by at least one of the monitoring stations, when this article travels past the sorting station.

Such a machine makes it possible to monitor at high speed the manufacture or production of transparent or translucent articles. To monitor the proper operation of the machine and sensors, it is known that the operator is wont, at regular time intervals, to feed in compliant and defective control or reference samples. These reference articles are inserted into the flow of inspected articles although the result, compliant or defective, is of course known. The operator thus checks that the compliant reference articles are not discarded by the machine and that the defective reference articles are indeed ejected.

Though this scheme makes it possible to detect the operating drift of the machine, this method does not give the operator any additional information in order to optimize the operation of the machine relating to its capacity to detect without error, the articles that are actually defective.

The object of the invention is therefore aimed at proposing a novel method making it possible to inspect with the aid of a machine transparent or translucent hollow articles streaming at high speed, this method making it possible to optimize the detection quality so as to reduce or indeed eliminate, the rejection of actually compliant articles considered to be defective by the machine and/or the non-detection of actually defective articles considered to be compliant by the machine.

To achieve such an objective, the method is aimed at inspecting, with the aid of a machine, transparent or translucent hollow articles streaming at high speed in succession, past a series of monitoring stations each comprising at least one sensor delivering an output signal for each article traveling past a sensor while considering that a sensor is able to see at least one article travel past before the previous article goes past the last sensor, the output signals being processed so as to determine a result indicating the compliant articles and the defective articles. The method consists in implementing at least one phase of assessing the setting of the machine consisting:

in choosing compliant and defective reference articles,
for each reference article, recording the output signals of the sensors with each of which are associated an identifier for the reference article concerned and an expected result regarding the compliant or defective character of the reference article,
in selecting together, during the processing of the signals, at least two recorded output signals corresponding to one and the same reference article, so as to obtain after processing, a result regarding the defective or compliant character of the reference articles,
and in comparing the result obtained by processing, regarding the defective or compliant character of each reference article with the expected result associated with each reference article so as to deduce the quality of setting of the machine.

By way of example, the method consists in choosing the reference articles from among gauge or control articles made to stream past the sensors or from among articles inspected in the course of the inspection phase.

For example, the method consists in processing the output signals associated with the reference articles with identical or different processing parameters from the parameters used for the processing of the output signals arising from the sensors past which the articles stream. Thus, the method consists in processing the output signals associated with the reference articles according to an identical or different setting from the setting used for the processing of the output signals arising from the sensors past which the articles stream.

For the articles inspected in the course of the inspection phase, the method consists:

in recording the output signals of the sensors, while associating with each of them an identifier for the article concerned,
and during the processing of the signals, in selecting together at least two recorded output signals corresponding to one and the same article, doing so for all the articles, so as to make it possible to take into account, by article, the output signals.

Advantageously, the method consists in carrying out a phase of assessing the setting of the machine during the phase of inspecting the articles.

According to an advantageous characteristic, the method consists in automatically and/or periodically carrying out a phase of assessing the setting of the machine.

According to another advantageous characteristic, the method consists on termination of the phase of assessing the setting of the machine, in having available a quality performance indicator for the machine giving the number of defective reference articles actually considered to be defective by the machine, and/or a productivity performance indicator for the machine giving the number of compliant reference articles actually considered to be compliant by the machine.

Another object of the invention is to propose a machine for inspecting transparent or translucent hollow articles streaming at high speed in succession, past a series of monitoring stations each comprising at least one sensor delivering an output signal for each article traveling past said sensor by considering that a sensor is able to see at least one article travel past before the previous article goes past the last sensor, the sensors being linked to a processing and monitoring unit adapted for processing the output signals so as to determine a result indicating the compliant articles and the defective articles, the processing and monitoring unit comprising storage means able to record at least output signals of the sensors and an article identifier for each output signal, associated with said article.

According to the invention, the storage means record output signals corresponding to compliant and defective reference articles, with each of these reference articles are associated an identifier for the reference article concerned and an expected result regarding the compliant or defective character of the reference article, the processing and monitoring unit comprising:

means for carrying out a phase of assessing the setting of the machine consisting in triggering, for each reference article, the processing of at least two output signals for this reference article, so as to obtain after processing, a result regarding the defective or compliant character of each reference article, means for comparing the result obtained regarding the defective or compliant character of each reference article with the expected result associated with each reference article so as to deduce therefrom the quality of setting of the machine.

To allow the inspection of the articles, the processing and monitoring unit comprises:

storage means able to record at least two output signals of the sensors and an article identifier for each output signal, associated with said article, means for selecting at least two recorded output signals corresponding to one and the same article, doing so for all the articles, and processing means adapted for taking into account together, for the processing, at least two of the recorded and selected output signals corresponding to one and the same article.

Advantageously, the machine comprises means for automatically carrying out a phase of assessing the setting of the machine.

Advantageously, the processing and monitoring unit comprises in the guise of setting of the machine, on the one hand parameters of the calculation or processing means for the output signals and on the other hand, quality criteria.

Advantageously, the machine comprises means for modifying the setting of the machine, that is to say processing parameters used for the processing of the articles.

Advantageously, the processing and monitoring unit comprises means adapted for processing at the same time according to different settings, the output signals recorded for reference articles, and output signals relating to articles streaming past the sensors.

According to an advantageous embodiment characteristic, the processing and monitoring unit comprises at least one quality performance indicator for the machine giving the number of defective reference articles actually considered to be defective by the machine, and/or a productivity performance indicator for the machine giving the number of compliant reference articles actually considered to be compliant by the machine.

According to another characteristic of the subject of the invention, the machine comprises at least one display screen linked to the processing and monitoring unit which provides the screen with at least two recorded output signals and/or with characteristic data corresponding to one and the same article so as to ensure the simultaneous display of the recorded output signals and/or characteristic data corresponding to one and the same article, and/or of the quality or productivity performance indicators.

Preferably, the machine comprises a station for sorting between the defective articles not adhering to the quality criteria and the compliant articles adhering to the quality criteria, this sorting station is placed following the last sensor while being linked to the processing and monitoring unit.

Diverse other characteristics emerge from the description given below with reference to the appended drawings which show, by way of nonlimiting examples, embodiments of the subject of the invention.

Figure 1:
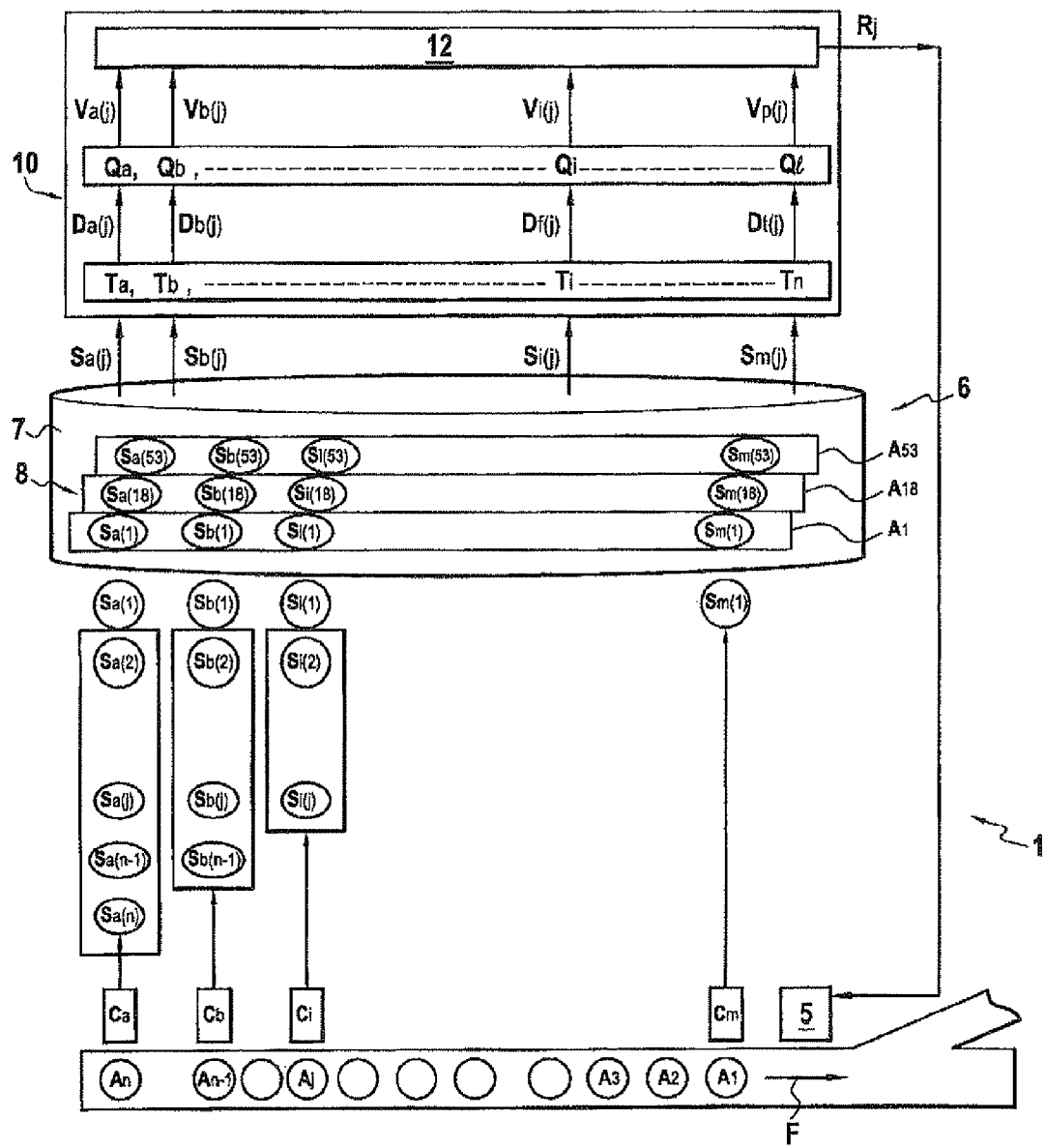
FIG. 1 is a general schematic view of a monitoring machine in accordance with the invention.

As emerges more precisely from FIG. 1, the subject of the invention relates to a machine 1 for inspecting transparent or translucent hollow articles $A_1, A_2 \ldots A_j \ldots A_n$ (with j varying from 1 to n), such as for example glass or plastic articles such as bottles, pots or jars. The machine 1 comprises a series of monitoring stations each comprising at least one sensor Ca, Cb..., Ci,... Cm (with i varying from a to m) and past which the articles Aj stream at high speed. The monitoring machine 1 thus comprises a conveyer 3 enabling the articles $A_1$, $A_2$, Aj..., An to be made to stream successively and respectively past the sensors Ca, Cb ..., Ci ..., Cm in the direction of streaming represented by the arrow F. This streaming is such that a sensor is able to see at least one article Aj travel past before the previous article Aj−1 goes past the last sensor namely Cm when considering the direction of streaming F. In the example illustrated, the direction of streaming of the articles is represented in a linear manner but it is clear that the subject of the invention applies for all types of displacement making the articles stream in succession past monitoring stations.

Each sensor Ci delivers an output signal Si(j) (with i varying from 1 to m) for each article Aj traveling past said sensor. In a conventional manner, the machine 1 comprises detection means such as presence sensors like photoelectric cells making it possible to detect the arrival of the article Aj opposite the sensor Ci and to trigger the acquisition of the signal Si(j) for the article Aj. Thus, when for example the article $A_1$ travels past the sensors for example Ca and Cm, these deliver an output signal respectively Sa(1) and Sm(1). Likewise, when, for example, the article $A_2$ travels past the sensors, for example Ca, Cb, these deliver an output signal respectively Sa(2) and Sb(2). Thus, it must be understood that the passage of each article Aj past the set of m sensors Ci leads to the obtaining of m signals Si(j) for each article Aj.

The sensors Ci can be of any nature adapted for ensuring inspection or monitoring of the articles Aj making it possible to determine whether or not these articles adhere to quality criteria, that is to say whether these articles are compliant or defective. For example, these sensors Ci are measurement sensors, image sensors, cameras. According to an advantageous variant embodiment at least two of the sensors Ci are image sensors.

The monitoring machine 1 preferably comprises a station 5 for sorting between the defective articles adhering to the quality criteria and the compliant articles adhering to said criteria. This sorting station 5 is placed behind the last sensor namely Cm, when considering the direction of streaming F. Stated otherwise, each article Aj travels past the sorting station 5 after having traveled past the last sensor Cm. For example, the sorting station 5 can comprise an ejector removing the defective articles from the queue of inspected articles.

The monitoring machine 1 also comprises a processing and monitoring unit 6 to which the sensors Ci and the sorting station 5 are linked. This processing and monitoring unit 6 comprises software and hardware means adapted for acquiring and processing the output signals Si(j) and for controlling the sorting station 5 as a function of the defective or non-defective character of the inspected articles. It should be noted that it must be understood that the processing and monitoring unit 6 does not necessarily correspond to a single apparatus such a computer composed of a central unit and of memories for example, but to various apparatuses linked together via communication links of all known types.

According to an advantageous characteristic of the subject of the invention, the processing and monitoring unit 6 comprise storage means 7 able to record at least the whole set of output signals Si(j) of the sensors Ci. It should be considered that the output signals Si(j) recorded correspond to the raw output signals delivered by the sensors Ci. Stated otherwise, these output signals Si(j) are recorded without having been processed.

These storage means 7 are able to also record an identifier j in association with each output signal Si(j). Indeed, the monitoring machine 1 comprises means for tracking the advance of the articles Aj past the monitoring and sorting stations. For example, these means for tracking the advance of the articles can be embodied as coders. Thus, each output signal Si(j) of the sensors Ci, for an article Aj, is recorded in association with an identifier j for the article Aj concerned. A database can thus be constructed grouping together the set of output signals Si(j) of the set of sensors Ci, these output signals Si(j) being assigned an identifier of articles to which they correspond. For example, a serial number j, a counter or any accurate date-stamp can be used as identifier.

The processing and monitoring unit 6 comprises means 8 for selecting at least two of the recorded output signals for example Si(j) and Sk(j) and corresponding to one and the same article Aj. Preferably, the set of output signals recorded Si(j) for one and the same article Aj are selected or grouped together. FIG. 1 shows diagrammatically, by way of example, the grouping of the signals Sa(1), Sb(1) ... Si(1) ... Sm(1) for the article $A_1$, of the output signals Sa(18), Sb(18) ... Si(18) ... Sm(18) for the article $A_{18}$ and of the output signals Sa(53), Sb(53) ... Si(53) ... Sm(53) for the article $A_{53}$. Preferably, the grouping of the output signals Si(j) by article is carried out for the set of n articles Aj. Of course, the grouping of the output signals Si(j) by article Aj, illustrated in FIG. 1 is merely a schematic representation not necessarily corresponding to the location of the output signals in the database.

It should be considered that the recorded output signals Si(j) thus selected by article Aj, can be taken into account together during the operation of processing the recorded output signals and which is intended to determine the compliant or non-compliant character of the articles. For this purpose, the processing and monitoring unit 6 comprises processing means 10, adapted for determining whether each article Aj is compliant or defective. These processing means 10 comprise calculation or processing means Ti (with i varying from a to n) for the recorded output signals Si(j) so as to obtain characteristic data Df(j) (with f varying from a to t). These characteristic data Df(j) are compared with quality criteria Qi (with i varying from a to I) making it possible to obtain one or more rankings or verdicts Vi(j) (with i varying from a to p) which are recovered with the aid of combination or analysis means 12 so as to obtain a result Rj regarding the article Aj. In a general way, the n processings Ti, the t characteristic data Df(j), the I quality criteria Qi and/or the p verdicts Vp(j) are equal in number or different in number from one another and with respect to the m output signals Sm(j).

Of course, the calculation or processing means Ti are adapted to the nature of the output signals Si(j) and to the quality criterion to be monitored. For example, if an output signal is an image, the calculation or processing means can perform geometry or photometry analyses, transformations of images by anamorphosis, etc.

According to a first exemplary implementation, each calculation or processing means Ti of the processing means 10 is applied to a recorded output signal Si(j) making it possible to obtain a characteristic datum. Stated otherwise, according to this exemplary embodiment, the processings Ti are performed, on the output signals Si(j) relating to one and the same article A(j), in a mutually independent manner. For example, a characteristic datum Df(j) can be a measurement such as for example a geometric characteristic of the article seen in the image. A characteristic datum Df(j) can be, for example, also, the presence of a defect such as an inclusion, a fold, an air bubble, the deformation of an ornament (or embellishment) or of a label, or the absence of a compulsory indication.

The calculation or processing means Ti are implemented so as to process substantially synchronously or simultaneously at least two output signals, for example Si(j), Sk(j) and preferably the set of recorded signals corresponding to one and the same article. Thus, for example the output signals Sa(1), Sb(1) ... Si(1) ... Sm(1) corresponding to the article $A_1$ are taken into account together for the processing, namely respectively by the calculation or processing means respectively Ta, Tb ... Ti ... Tn. The output signals Si(j) corresponding to one and the same article Aj are therefore processed together or substantially simultaneously.

According to this example, the set of processings carried out on the output signals of one and the same article makes it possible to obtain, substantially synchronously or simultaneously, characteristic data Df(j) which are compared with quality criteria Qi. Thus the set of comparisons for one and the same article between the characteristic data Df(j) and the quality criteria Qi occurs substantially simultaneously or synchronously. For example, the quality criteria Qi correspond to thresholds fixing the limit between a compliant article and a defective article. These thresholds can correspond for example to dimensions of the article, material distributions, the presence of dirt, inclusions, air bubbles, or to a number of air bubbles.

Comparison between the characteristic data Df(j) and the quality criteria Qi makes it possible to obtain a ranking or a verdict Vi(j) corresponding to a defective or compliant article Aj. It should be noted that for each article Aj, the verdicts or rankings Vi(j) can be obtained together or in a synchronous manner permitting a per-article consolidation processing 12 of the verdicts or rankings. The availability of the verdicts or rankings relating to one and the same article enables the set of verdicts or rankings Vi(j) relating to the article to be taken into account simultaneously or synchronously, making it possible to deduce therefrom a result Rj regarding the article concerned Aj. Stated otherwise, for one and the same article, the ranking Vi(j) obtained subsequent to the application of a quality criterion Qi can be modified by taking account of the ranking Vk(j) obtained subsequent to the application of another quality criterion Qk. Thus, taking the verdicts or ranking relating to an article into account together makes it possible to modify or to consolidate the individual verdicts or rankings obtained for this article.

The result Rj regarding the article concerned Aj is transmitted to the sorting station 5 so that the latter can remove each defective article Aj from the queue when said article travels past the sorting station 5.

It emerges from the preceding description that the recording of the output signals Si(j) of the sensors makes it possible, when processing these signals, to take into account several or the whole set of output signals relating to one and the same article Aj, independently of the order of output of the output signals Si(j). This availability makes it possible to mutually consolidate the verdicts.

According to another exemplary embodiment, it appears possible to take into account for each article Aj, at least two and in general the whole set of output signals Si(j) relating to one and the same article, making it possible to obtain for each article, after processing, characteristic data Dt(j) resulting from the combined analysis of these output signals. According to this variant embodiment, the calculation or processing means Ti for each output signal Si(j) interact with one another or are not mutually independent.

For example, it can be envisaged that the processing of an output signal of an article depends on the result of at least one other processing of another output signal relating to said article. Thus, the processing for example Tb of the output signal Sb(1) of the article $A_1$ may be performed only after the execution of the processing for example Tc of the output signal Sc(1) of the article $A_1$. Stated otherwise, the result of the processing Tc must be known in order to perform the processing Tb.

It should be noted that, having regard to the recording of the output signals, the order of processing of the output signals relating to one and the same article may be different from the order of acquisition of these output signals.

According to another example, taking at least two and in general all the output signals Si(j) relating to one and the same article into account together makes it possible to implement a combination processing for combining these output signals so as to obtain characteristic data Dt(j). The output signals relating to one and the same article are thus processed in a combined manner making it possible to implement for example operations of comparison, subtraction, addition, correlation, etc.

It should be noted that these characteristic data Dt(j) obtained after processing, are in number per article, greater than, equal to or less than the number of output signals Si(j) per article. Indeed, the combined processing of the output signals Si(j) makes it possible to obtain additional information and/or to reduce the number of characteristic data Dt(j) with respect to the output signals Si(j).

As explained above, the characteristic data Df(j) are compared with the quality criteria Qi so as to obtain a number i of verdicts or of rankings Vi(j) corresponding to a defective or compliant article Aj. The taking into account by means 12, of the verdicts Vi(j) for one and the same article makes it possible to deduce therefrom a result Rj regarding the article concerned. It should be noted that the means 12 are able to take into account the verdicts Vi(j) in an independent manner (so that one verdict does not influence another verdict) or in a dependent manner so as to consolidate or modify the result Rj.

In accordance with the invention, the object of the invention is aimed at implementing at least one phase of assessing the setting of the machine during the inspection or monitoring phase for a batch of articles.

Figure 2:
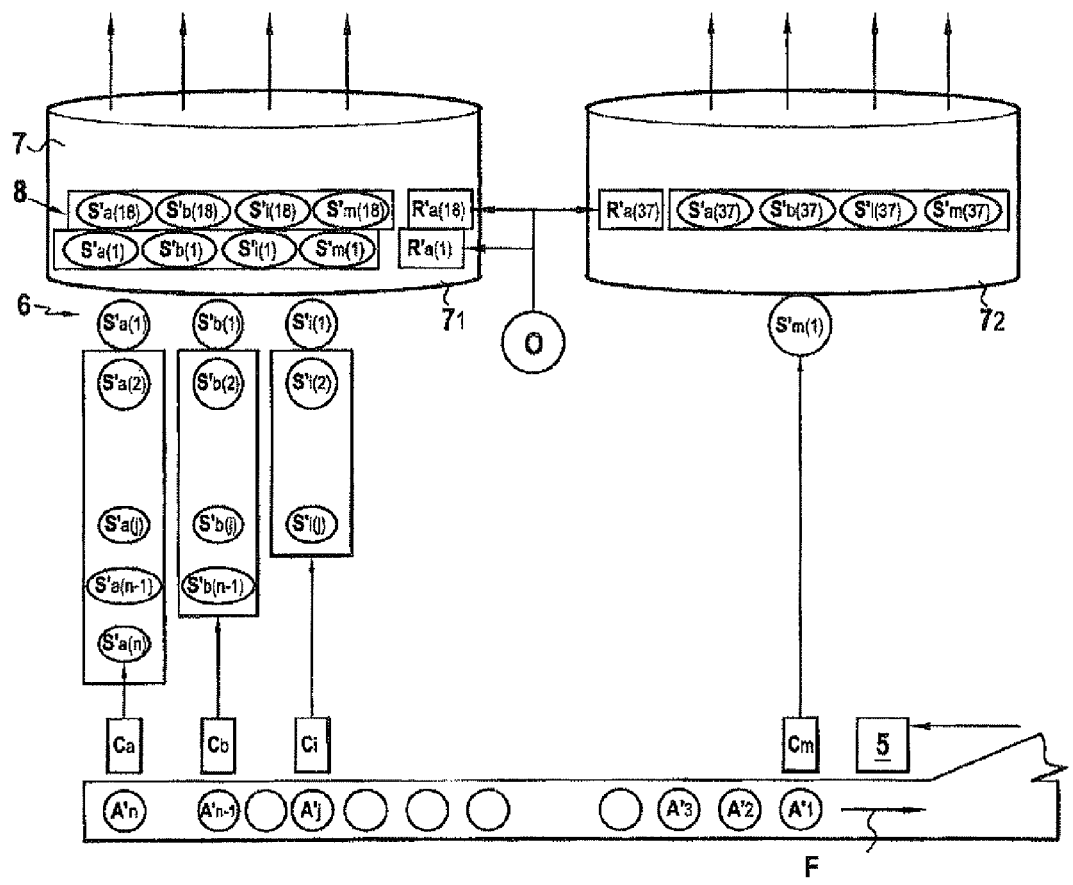
FIG. 2 is a schematic view showing a step of a phase of assessing the setting of the machine.

To implement such a phase of assessing the setting of the machine, there is provision, as illustrated in FIG. 2, to choose compliant and defective reference articles A'(j), the traveling of which past the various sensors Ci makes it possible to obtain output signals S'i(j) which are recorded in the storage means 7. With each recorded output signal are associated an identifier for the reference article concerned and an expected ranking R'aj regarding the compliant or defective character of the reference article. Indeed, the operator knows the result regarding the compliant or defective character of each of these reference articles. The operator O provides the machine with the expected results R'aj for these reference articles. As emerges from FIG. 2, it is for example possible to construct a database $7_1$ of the output signals corresponding to the compliant articles and a database $7_2$ of the output signals relating to the defective articles.

Figure 3:
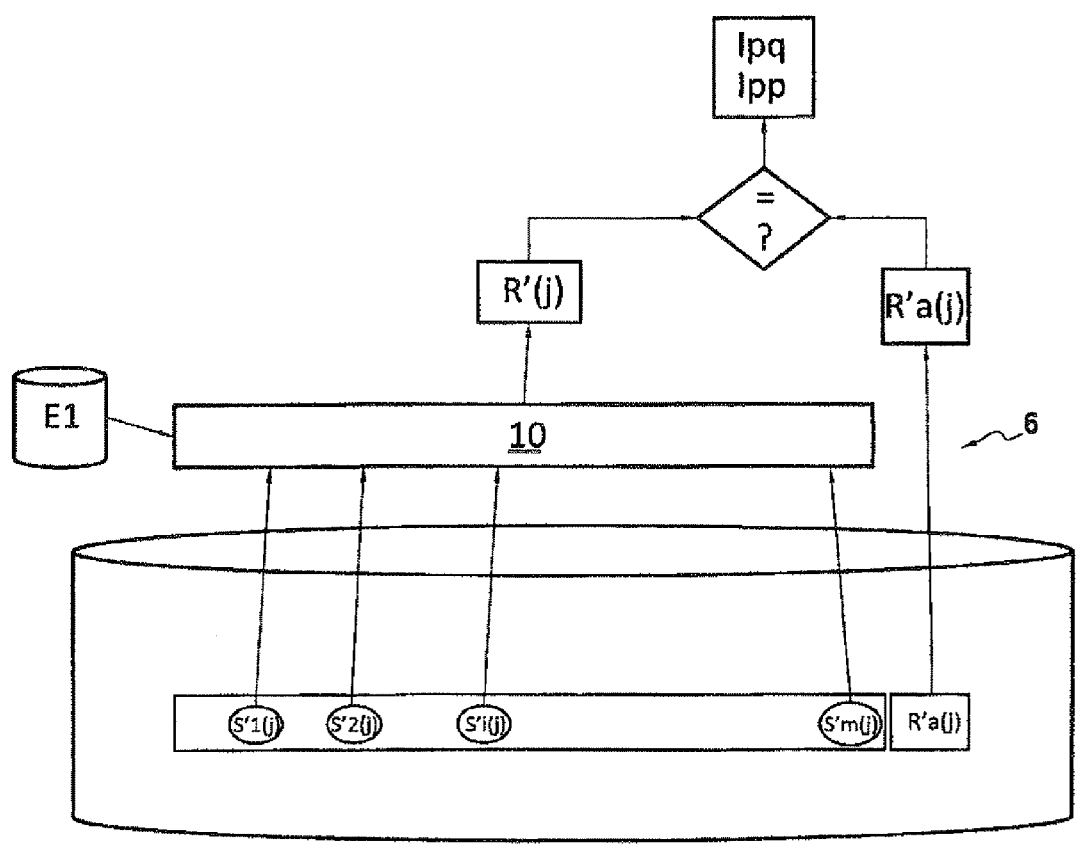
FIG. 3 is a schematic view explaining another step characteristic of a phase of assessing the setting of the machine.

As explained in relation to FIG. 1, during the processing of these output signals, by the means 10, at least two and in general the whole set of output signals relating to one and the same reference article are selected together. As illustrated in FIG. 3, this result obtained R'j by this processing 10, regarding the defective or compliant character of each reference article is compared with the expected ranking R'aj associated with the reference article so as to deduce therefrom the quality of setting of the machine, as a function of the agreement or otherwise between the result obtained R'j and the expected result R'aj.

The quality of setting of the machine can thus be expressed by a quality performance indicator Ipq for the machine and/or a productivity performance indicator Ipp for the machine.

The quality performance indicator Ipq is obtained by establishing the ratio between on the one hand, the number of defective reference articles A'j actually considered to be defective by the machine (that is to say the number of times that, for defective articles, the result obtained R'j is equal to the expected result R'aj) and on the other hand, the number of defective reference articles A'j.

Likewise, the productivity performance indicator Ipp for the machine is obtained by establishing the ratio between on the one hand, the number of compliant reference articles A'j actually considered to be compliant by the machine (that is to say the number of times that, for compliant articles, the result obtained R'j is equal to the expected result R'aj) and on the other hand, the number of compliant reference articles A'j.

Each quality performance indicator Ipq or productivity performance indicator Ipp can be expressed as a percentage or can form the subject of a visualization or of an appropriate display.

According to a first exemplary embodiment, the reference articles are chosen from among gauge articles or control articles which are placed by the operator so as to stream past the sensors, during a machine setting phase. The traveling of the control articles past the sensors makes it possible to obtain output signals which are recorded with the ranking compliant or defective. These output signals indexed by reference articles and with which the expected ranking R'aj is associated can be used by the operator each time that a phase of assessing the setting of the machine is necessary.

According to a second exemplary embodiment, the reference articles A'j are chosen from among the articles Aj previously inspected. Stated otherwise, it is possible to chose as reference articles, a batch of articles taken from among part or indeed the entirety of the articles Aj previously inspected. In a more precise manner, the operator in fact selects the output signals recorded Si(j) during the monitoring of production and indexed by article. A compliant or defective ranking R'aj is ascribed to these recorded output signals Si(j) that may be assessed as virtual samples in such a way that they constitute reference articles.

It should be understood that in the examples described above, the output signals recorded and assigned a ranking can be used as and when the need arises, for the phase of assessing the setting of the machine. Indeed, the machine can regularly or periodically and in an automatic manner without the intervention of the operator, undertake this phase of assessing the setting of the machine. Moreover, the machine can communicate via a supervision network, in addition to the statistical results of the inspection in progress, the results Ipq, Ipp of assessing the setting of the machine. The machine can trigger an alert signal if this assessment reveals a drift.

It is thus possible to simulate on the monitoring machine by replaying the recorded output signals relating to these reference articles, the traveling past of a set of reference articles so that it is possible to have available the quality performance indicator Ipq for the machine and/or a productivity performance indicator Ipp for the machine.

These two indicators make it possible to describe in a very overall manner the performance of the machine and to compare over time on the basis of the same information, any alterations or drift in the behavior of the machine. These two indicators can be communicated via the supervision network.

It should be noted that these performance indicators are fair since they rely on taking account of the articles and not of the partially stored and/or identifier-less signals as is proposed by the prior art. Thus, if two output signals delivered by two sensors lead to two verdicts of defects for the same article, the method does not log two defective articles.

According to another advantageous characteristic of the subject of the invention, the phase of assessing the setting of the machine is carried out during or simultaneously with the phase of monitoring the articles Aj. For this purpose and as emerges more precisely from FIG. 4, the processing and monitoring unit 6 is dimensioned so as to be able simultaneously on the one hand, to monitor the articles Aj streaming past the sensors Ci and on the other hand, to undertake the processing, per article, of the recorded output signals S'i(j) for the reference articles, so as to assess the setting of the machine.

Insofar as the monitoring machine 1 has the capacity to process a genuine production of reference articles while continuing to perform its inspection work, the operator in charge of setting the machine has means for helping him to optimize the performance of the machine. Thus, the operator can with complete assurance, modify the setting of his machine, estimate the relevance of this new setting without disturbing the on-line monitoring performed by the machine. For this purpose, the processing means 10 use test data or parameters which are different from the data or parameters used for the processing of the output signals from the sensors past which the articles Aj stream.

Figure 4:
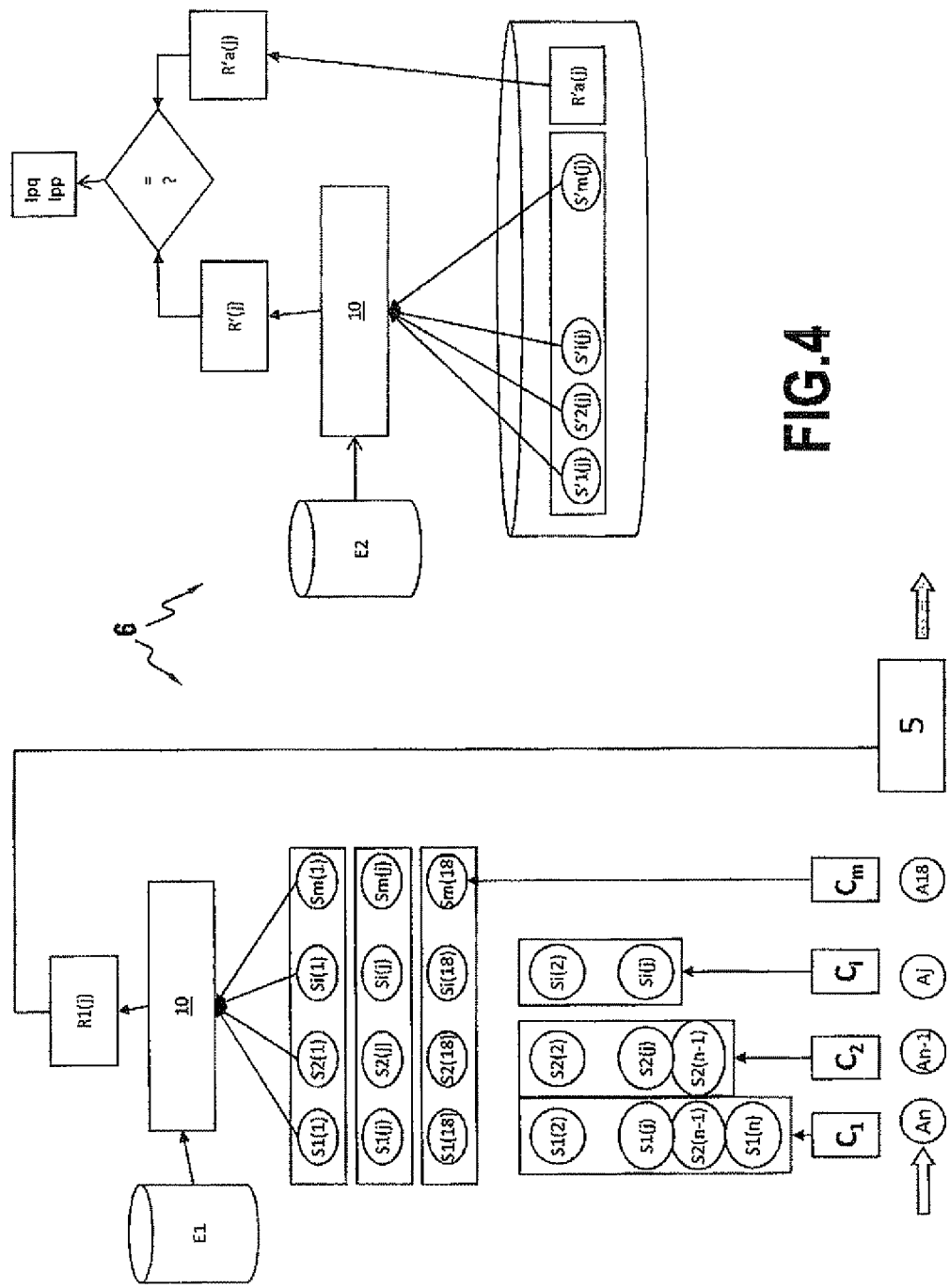
FIG. 4 is a schematic view showing another exemplary implementation of a phase of assessing the setting of the machine, in parallel with a detection phase.

FIG. 4 illustrates in a schematic manner the operation of the processing means 10 according to a setting $E_1$ of the machine. As explained above, such a setting $E_1$ consists in the choice or in the determination of the parameters of the calculation or processing means Ti and/or of the quality criteria Qi. For example, the operation of setting the parameters of the calculation or processing means Ti can consist of a modification of threshold, of the gain of a digital amplifier or in the case of image processing, in the modification of the zones of interest or digital filters. For example, the operation of setting the quality criteria Qi can consist in modifying tolerances of height for example or the maximum surface area of the defects. It should be noted that the implementation of the inspection phase or of the phase of assessing the setting according to a setting $E_1$ makes it possible to associate performance indicators Ipp, Ipq therewith.

In parallel with the processing of the articles Aj by the machine, the operator can with complete assurance, create a new setting $E_2$ of the machine, that is to say a new suite of parameters for the processing and calculation means Ti. For this new setting $E_2$, new performance indicators Ipp, Ipq are obtained. The operator can estimate the performance of the setting $E_2$ by virtue of the calculations of the performance indicators Ipp, Ipq on the reference articles whose output signals have been recorded, while letting the machine continue in parallel the on-line inspection of the articles with the processing means and the suite of current parameters (setting $E_3$). If the operator observes that the new setting $E_2$ is better than the current setting $E_1$, on the basis of a comparison in particular of the performance indicators Ipp, Ipq according to the settings $E_1$, $E_2$, he can then instantaneously replace the current setting with the new setting so that subsequently, the on-line production is inspected with the new setting.

If the operator wants to modify the machine setting parameters, he can apply them to all or part of the already inspected production.

The operator thus has statistical information regarding the quality of his new setting $E_2$ and is capable of predicting the effects of this new setting:
  improvement or degradation of the detection of defects (rate of defective articles) and in what proportion,
  improvement or degradation of the production level of the inspection line (rate of compliant articles) and in what proportion.

According to another advantageous characteristic of the subject of the invention, the processing and monitoring unit 6 is linked to a display screen adapted for ensuring the simultaneous display of the recorded output signals Si(j) corresponding to one and the same article and/or of the characteristic data Dt(j) corresponding to one and the same article. Preferably, the operator controls the processing and monitoring unit 6 so that the latter delivers the selected signals to the screen. The screen thus simultaneously displays the signals relating to one and the same article, thus making it possible to best characterize a predetermined article. Of course, the screen is able to display the signals relating to any article Aj. This simultaneous display of the signals for any inspected article, at the request of the operator, is particularly advantageous in the case of image sensors, since the screen displays all the views of an article obtained from different angles by various image sensors (or cameras). Moreover, the screen is adapted for ensuring the display of the quality performance indicator Ipq and productivity indicator Ipp for the machine, in all possible forms, such as graphical or digital.

In the same sense, the processing and monitoring unit 6 is able to provide remotely, via a communication network, the recorded output signals Si(j) and/or characteristic data Dt(j) corresponding to one and the same article and/or the quality performance indicator Ipq or productivity performance indicator Ipp.

The invention is not limited to the examples described and represented since various modifications may be made thereto without departing from the scope thereof.

The invention claimed is:

1. A method for inspecting, with the aid of a machine (1), transparent or translucent hollow articles (Aj) streaming at high speed in succession, past a series of monitoring stations each comprising at least one sensor (Ci) delivering an output signal (Si(j)) for each article (Aj) traveling past a sensor by considering that a sensor is able to see at least one article (Aj) travel past before the previous article (Aj−1) goes past the last sensor, the output signals (Si(j)) being processed so as to determine a result (Rj) indicating the compliant articles and the defective articles, characterized in that it consists in implementing at least one phase of assessing the setting of the machine consisting:

in choosing compliant and defective reference articles (A'(j)), for each reference article (A'(j)), recording the output signals (S'i(j)) of the sensors with each of which are associated an identifier for the reference article concerned and an expected result (R'a(j)) regarding the compliant or defective character of the reference article, in selecting together, during the processing of the signals, at least two recorded output signals [S'a(j)], [S'k(j)] corresponding to one and the same reference article, so as to obtain after processing, a result (R'j) regarding the defective or compliant character of the reference articles (A'j), and in comparing the result obtained by processing (R'j), regarding the defective or compliant character of each reference article with the expected result (Ra'(j)) associated with each reference article so as to deduce the quality of setting of the machine; and, further characterized in that it consists for the articles (Aj) inspected in the course of the inspection phase:

in recording the output signals (Si(j)) of the sensors (Ci), while associating with each of them an identifier (j) for the article concerned (Aj), and during the processing of the signals, in selecting together at least two recorded output signals (Si(j), Sk(i)) corresponding to one and the same article, doing so for all the articles, so as to make it possible to take into account, by article (Aj), the output signals (Si(j), Sk(j)).

2. The method as claimed in claim 1, characterized in that it consists in choosing the reference articles (A'j) from among gauge or control articles, made to stream past the sensors or from among articles (Aj) inspected in the course of the inspection phase.

3. The method as claimed in claim 1, characterized in that it consists in processing the output signals (S'i(j)) associated with the reference articles according to an identical or different setting from the setting used for the processing of the output signals (Si(j)) arising from the sensors past which the articles (A'j) stream.

4. The method as claimed in claim 1, characterized in that it consists in carrying out a phase of assessing the setting of the machine during the phase of inspecting the articles (Aj).

5. The method as claimed in claim 1, characterized in that it consists in automatically and/or periodically carrying out a phase of assessing the setting of the machine.

6. The method as claimed in claim 1, characterized in that it consists on termination of the phase of assessing the setting of the machine, in having available a quality performance indicator (Ipq) for the machine giving the number of defective reference articles actually considered to be defective by the machine, and/or a productivity performance indicator (Ipp) for the machine giving the number of compliant reference articles actually considered to be compliant by the machine.

7. A machine for inspecting transparent or translucent hollow articles (Aj) streaming at high speed in succession, past a series of monitoring stations each comprising at least one sensor delivering an output signal (Si(j)) for each article (Aj) traveling past said sensor by considering that a sensor is able to see at least one article (Aj) travel past before the previous article (Aj−1) goes past the last sensor, the sensors being linked to a processing and monitoring unit (6) adapted for processing the output signals so as to determine a result (Rj) indicating the compliant articles and the defective articles, the processing and monitoring unit (6) comprising storage means (7) able to record at least output signals (Si(j)) of the sensors (Ci) and an article identifier (j) for each output signal (Si(j)), associated with said article, characterized in that the storage means (7) record output signals (S'i(j)) corresponding to compliant and defective reference articles (A'i(j)), with each of these reference articles are associated an identifier (j) for the reference article concerned and an expected result (R'a(j)) regarding the compliant or defective character of the reference article and in that the processing and monitoring unit (6) comprises:

means for carrying out a phase of assessing the setting of the machine consisting in triggering, for each reference article (A'j), the processing of at least two output signals [S'i(j),S'k(j)] for this reference article, so as to obtain after processing, a result (R'j) regarding the defective or compliant character of each reference article (A'j), means for comparing the result (R'j) obtained regarding the defective or compliant character of each reference article with the expected result (R'a(j)) associated with each reference article so as to deduce therefrom the quality of setting of the machine; and characterized in that the processing and monitoring unit (6) comprises in the guise of setting of the machine, on the one hand the parameters of the calculation or processing means (Ti) for the output signals and on the other hand, quality criteria (Qi).

8. The machine as claimed in claim 7, characterized in that the processing and monitoring unit (6) comprises:

storage means (7) able to record at least two output signals [Si(j),Sk(j)] of the sensors (Ci) and an article identifier for each output signal (Si(j)), associated with said article, means for selecting at least two recorded output signals [Si(j),Sk(j)] corresponding to one and the same article, doing so for all the articles, and processing means adapted for taking into account together, for the processing, at least two of the recorded and selected output signals [Si(j),Sk(j)] corresponding to one and the same article.

9. The machine as claimed in claim 7, characterized in that it comprises means for modifying the setting of the machine.

10. The machine as claimed in claim 9, characterized in that the processing and monitoring unit (6) comprises means adapted for processing at the same time, according to different settings respectively ($E_2$, $E_1$), the output signals recorded for reference articles (A'j), and output signals relating to articles (Aj) streaming past the sensors.

11. The machine as claimed in claim 7, characterized in that the processing and monitoring unit (6) comprises means for determining at least one quality performance indicator (Ipq) for the machine giving the number of defective reference articles actually considered to be defective by the machine, and/or a productivity performance indicator (Ipp) for the machine giving the number of compliant reference articles actually considered to be compliant by the machine.

12. The machine as claimed in claim 7, characterized in that it comprises at least one display screen linked to the processing and monitoring unit (6) which provides the screen with at least two recorded output signals [Si(j),Sk(j)] and/or with characteristic data Dt(j) corresponding to one and the same article so as to ensure the simultaneous display of the recorded output signals and/or characteristic data corresponding to one and the same article, and/or of the quality performance (Ipq) or productivity performance indicators (Ipp).

13. The machine as claimed in claim 7, characterized in that it comprises means for automatically and/or periodically carrying out the phase of assessing the setting of the machine.

14. The machine as claimed in claim 7, characterized in that it comprises a station (5) for sorting between the defective articles not adhering to the quality criteria and the compliant articles adhering to the quality criteria, this sorting station (5) is placed following the last sensor while being linked to the processing and monitoring unit (6).

15. The machine as claimed in claim 7, characterized in that the processing and monitoring unit (6) provides remotely, via a communication network, the output signals [Si(j)] and/or the characteristic data [Dt(j)] corresponding to one and the same article and/or the quality performance (Ipq) or productivity performance (Ipp) indicators.

\* \* \* \* \*

UNITED STATES PATENT AND TRADEMARK OFFICE
CERTIFICATE OF CORRECTION

PATENT NO. : 8,522,982 B2  Page 1 of 1
APPLICATION NO. : 12/599359
DATED : September 3, 2013
INVENTOR(S) : Venaille et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 778 days.

Signed and Sealed this

Fifteenth Day of September, 2015

Michelle K. Lee
*Director of the United States Patent and Trademark Office*